US010641783B2

(12) United States Patent
Lynn et al.

(10) Patent No.: US 10,641,783 B2
(45) Date of Patent: May 5, 2020

(54) METHOD AND APPARATUS FOR DETECTING ACUTE USE OF TARGET SUBSTANCE(S)

(71) Applicant: Hound Labs, Inc., Oakland, CA (US)

(72) Inventors: Michael Scott Lynn, Piedmont, CA (US); Seong-Kun Oh, Piedmont, CA (US)

(73) Assignee: Hound Labs, Inc., Oakland, CA (US)

( * ) Notice: Subject to any disclaimer, the term of this patent is extended or adjusted under 35 U.S.C. 154(b) by 181 days.

(21) Appl. No.: 15/958,616

(22) Filed: Apr. 20, 2018

(65) Prior Publication Data

US 2018/0238916 A1  Aug. 23, 2018

Related U.S. Application Data

(63) Continuation of application No. 14/641,412, filed on Mar. 8, 2015, now Pat. No. 9,970,950.

(60) Provisional application No. 61/950,173, filed on Mar. 9, 2014.

(51) Int. Cl.
   *G01N 33/94*   (2006.01)
   *G01N 33/557*   (2006.01)

(52) U.S. Cl.
   CPC ......... *G01N 33/948* (2013.01); *G01N 33/557* (2013.01)

(58) Field of Classification Search
   CPC ........................... G01N 33/948; G01N 33/557
   See application file for complete search history.

(56) References Cited

U.S. PATENT DOCUMENTS

| | | |
|---|---|---|
| 3,086,833 A | 4/1963 | Streck |
| 3,676,072 A | 7/1972 | Krivis |
| 4,288,344 A | 9/1981 | Reiss |
| 4,771,005 A | 9/1988 | Spiro |
| 5,361,771 A | 11/1994 | Craine et al. |
| 5,922,610 A | 7/1999 | Alving et al. |
| 6,605,444 B1 | 8/2003 | Klein et al. |
| 8,707,758 B2 | 4/2014 | Keays |
| 9,709,581 B1 | 7/2017 | Gordon et al. |
| 9,709,582 B1 | 7/2017 | Gordon et al. |
| 9,726,684 B1 | 8/2017 | Gordon et al. |
| 9,921,234 B1 | 3/2018 | Lynn et al. |
| 9,933,445 B1 | 4/2018 | Lynn et al. |
| 9,945,878 B1 | 4/2018 | Gordon et al. |
| 2002/0177232 A1 | 11/2002 | Melker et al. |
| 2003/0153844 A1 | 8/2003 | Smith |
| 2004/0043479 A1 | 3/2004 | Briscoe et al. |

(Continued)

FOREIGN PATENT DOCUMENTS

| | | |
|---|---|---|
| EP | 132313 | 9/1991 |
| EP | 2781917 | 9/2014 |
| WO | 2006/083269 | 8/2006 |

OTHER PUBLICATIONS

U.S. Appl. No. 14/997,405, Notice of Allowance dated May 10, 2017.

(Continued)

*Primary Examiner* — Dennis White
(74) *Attorney, Agent, or Firm* — Carr & Ferrell LLP

(57) ABSTRACT

Methods and devices for sampling, processing and identifying acute use of a substance or substances of abuse are provided. Systems and kits for sampling, processing and identifying acute use of a substance of abuse is also provided.

20 Claims, 4 Drawing Sheets

(56) References Cited

U.S. PATENT DOCUMENTS

| | | |
|---|---|---|
| 2005/0105077 A1 | 5/2005 | Padmanabhan et al. |
| 2005/0137491 A1 | 6/2005 | Paz et al. |
| 2007/0077660 A1 | 4/2007 | Glas |
| 2008/0004542 A1 | 1/2008 | Allen et al. |
| 2009/0017555 A1 | 1/2009 | Jehanli et al. |
| 2011/0086364 A1 | 4/2011 | Takkinen et al. |
| 2012/0302907 A1* | 11/2012 | Palmskog .............. A61B 5/082 600/532 |
| 2013/0006068 A1 | 1/2013 | Gemer et al. |
| 2013/0021153 A1 | 1/2013 | Keays |
| 2014/0288454 A1 | 9/2014 | Paz et al. |
| 2014/0366609 A1 | 12/2014 | Beck et al. |
| 2015/0305651 A1 | 10/2015 | Attariwala et al. |

OTHER PUBLICATIONS

U.S. Appl. No. 14/997,405, Office Action dated Jan. 9, 2017.
U.S. Appl. No. 14/997,405, Corrected Notice of Allowability dated Jun. 15, 2017.
U.S. Appl. No. 15/143,379, Office Action dated Oct. 25, 2016.
U.S. Appl. No. 15/143,379, Notice of Allowance dated Mar. 21, 2017.
U.S. Appl. No. 15/143,379, Notice of Allowability dated Jun. 13, 2017.
U.S. Appl. No. 15/143,328, Office Action dated Sep. 1, 2016.
U.S. Appl. No. 15/143,328, Notice of Allowance dated Feb. 10, 2017.
U.S. Appl. No. 15/143,328, Notice of Allowability dated May 18, 2017.
U.S. Appl. No. 15/143,328, Notice of Allowance dated Jun. 14, 2017.
U.S. Appl. No. 15/650,518, Office Action dated Oct. 4, 2017.
U.S. Appl. No. 15/650,518, Notice of Allowance dated Feb. 1, 2018.
U.S. Appl. No. 15/217,151, Office Action dated Jan. 9, 2017.
U.S. Appl. No. 15/217,151, Office Action dated May 16, 2017.
U.S. Appl. No. 15/217,151, Final Office Action dated Oct. 30, 2017.
U.S. Appl. No. 15/217,151, Notice of Allowance dated Dec. 22, 2017.
U.S. Appl. No. 15/217,264, Office Action dated Oct. 24, 2016.
U.S. Appl. No. 15/217,264, Office Action dated Mar. 20, 2017.
U.S. Appl. No. 15/217,264, Final Office Action dated Aug. 16, 2017.
U.S. Appl. No. 15/217,264, Notice of Allowance dated Nov. 16, 2017.
Adams, I.B. et al., "Cannabis: pharmacology and toxicology in animals and humans," Addiction, Nov. 1996;91 (11):1585-614, PubMed abstract 8972919.
Al-Asmari, Ahmed et al., "Method for the quantification of diamorphine and its metabolites in pediatric plasma samples by liquid chromatography-tandem mass spectrometry," Journal of Analytical Toxicology, vol. 34, May 2010.
Atkinson, H.C. et al., "Drugs in human milk. Clinical pharmacokinetic considerations." Clin Pharmacokinet. Apr. 1988;14(4):217-40, PubMed abstract 3292101.
Azorlosa, J.L. et al., "Marijuana smoking: effect of varying delta 9-tetrahydrocannabinol content and number of puffs," J. Pharmacol. Exper. Ther 1992;261:114, abstract.
Bailey, J.R. et al., "Fetal disposition of delta 9-tetrahydrocannabinol (THC) during late pegnancy in the rhesus monkey," Toxicol Appl Pharmacol. Sep. 15, 1987;90(2):315-21, abstract.
Baker, D. et al., "Cannabinoids control spasticity and tremor in a multiple sclerosis model," Nature, Mar. 2, 2000;404(6773):84-7, abstract.
Balabanova, S. et al., "Detection of drugs in sweat," Belt Gerichtl Med. 1990;48:45-9, abstract.
Bashir, W. et al., "Spectrophotometric Determination of Acetone in Acetic Acid", Microchemical Journal, 1983, 28, pp. 77-81.
Beck, Olof et al., "Detection of Delta9-tetrahydrocannabinol in exhaled breath collected from cannabis users," Journal of Analytical Toxicology, vol. 35, Oct. 2011.

Benowitz, Neal L. et al., "Metabolic and psychophysiologic studies of cannabidiol-hexobarbital interaction," Clinical Pharmacology and Therapeutics (1980) 28, 115-120, abstract.
Blanc, Jennifer A. et al., "Adsorption losses from urine-based cannabinoid calibrators during routine use," Clin. Chem. 39/8, 1705-1712 (1993).
Bloom, A.S., Effect of delta9-tetrahydrocannabinol on the synthesis of dopamine and norepinephrine in mouse brain synaptosomes, J Pharmocol Exp Ther. Apr. 1982;221(1):97-103.
Bornheim, Lester M. et al., "Characterization of cytochrome P450 3A inactivation by cannabidiol: possible involvement of cannabidiol-hydroxyquinone as a P450 inactivator," Chem. Res. Toxicol., 1998, 11 (10), pp. 1209-0450.
Bornheim, L.M. et al., "Human hepatic microsomal metabolism of delta 1-tetrahydrocannabinol," Drug Metab Dispos. Mar.-Apr. 1992;20(2):241-6, PubMed abstract 1352216.
Brenneisen, R. et al., "The effect of orally and rectally administered delta 9-tetrahydrocannabinol on spaticity: a pilot study with 2 patients," Int J Clin Pharmocol Ther. Oct. 1996;34(10):446-52.
Brunet, B. et al., "Validation of large white pig as an animal model for the study of cannabinoids metabolism: application to the study of THC distribution in issues," Forensic Sci Int. Sep. 12, 1996;161(2-3):169-74, PubMed abstract 16859848.
Burstein, S. et al., "Isolation and characterization of two major urinary metabolites of 1-tetrahydrocannabinol," Science, Apr. 28, 1972;176(4033):422-3, PubMed abstract 5026162.
Cami, J. et al., "Effect of subject expectancy on the THC intoxication and disposition from smoked hashish cigarettes," Pharmacology Biochemistry and Behavior, vol. 40, Issue 1, Sep. 1991, pp. 115-119.
Challapalli, P.V. et al., "In vitro experiment optimization for measuring tetrahydrocannabinol skin permeation," Int J Pharm. Jul. 25, 2002;241(2):329-39, PubMed abstract 12100860.
Chaturvedi, Arvind K., "Postmortem aviation forensic toxicology: an overview," Journal of Analytical Toxicology, vol. 34, May 2010.
"The Chemistry of Phenols," Zvi Rappoport, editor, © 2003 John Wiley & Sons, Ltd. ISBN: 0-471-49737-1.
Chiang, C. Nora et al., "Prenatal drug exposure: kinetics and dynamics," NIDA Research Monograph 60, 1985.
Christophersen, Asbjorg Solberg et al., "Tetrahydrocannabinol stability in whole blood: plastic versus glass containers," Journal of Analytical Toxicology, vol. 10, Jul./Aug. 1986.
Cirimele, V. et al., "Testing human hair for cannabis. III. Rapid screening procedure for the simultaneous identification of delta9-tetrahydrocannabinol, cannabinol, and cannabidiol," Journal of Analytical Toxicology, vol. 20, Jan./Feb. 1996.
Cone, Edward J. et al., "In vivo adulteration: excess fluid ingestion causes false-negative marijuana and cocaine urine test results," Journal of Analytical Toxicology, vol. 22, Oct. 1998.
Cone, Edward J. et al., "Marijuana-laced brownies: behavioral effects, physiologic effects, and urinalysis in humans following ingestion," Journal of Analytical Toxicology, vol. 12, Jul./Aug. 1988.
Cone, Edward J. et al., "Passive inhalation of marijuana smoke: urinalysis and room air levels of delta-9-tetrahydrocannabinol," Juornal of Analytical Toxicology, vol. 11, May/Jun. 1987.
Crouch, Dennis J. et al., "An evaluation of selected oral fluid point-of-collection drug-testing devices," Journal of Analytical Toxicology, vol. 29, May/Jun. 2005.
Crouch, D.J., "Oral fluid collection: the neglected variable in oral fluid testing," Forensic Sci Int. Jun. 10, 2005;150(2-3):165-73, PubMed abstract 15899565.
Day, David et al., "Detection of THCA in oral fluid by GC-MS-MS," Journal of Analytical Toxicology, vol. 30, Nov./Dec. 2006.
D'Sourza, Deepak Cyril et al., "The psychotomimetic effects of intravenous delta-9-tetrahydrocannabinol in healthy individuals: implications for psychosis," Neuropsychopharmacology (2004) 29, 1558-1572.
Ellis, G.M. Jr. et al., "Excretion patterns of cannabiniod metabolites after last use in a group of chronic users," Clin Pharmacol Ther. Nov. 1985;38(5):572-8, PubMed abstract 3902318.

(56) References Cited

OTHER PUBLICATIONS

Ellis, George M. Jr. et al. "Excretion patterns of cannabinoid metabilites after last use," 420 Magazine, Oct. 4, 2011, downloaded from https://www.420magazine.com/forums/drug-testing-urine/153724.

ElSohly, M. et al., "Potency trends of Delta9-THC and other cannabinoids in confiscated marijuana from 1980-1997," Journal of Forensic Sciences, vol. 45, No. 1, 2000, pp. 24-30.

Feng, Shixia et al., "Simultaneous analysis of Delta9-THC and its major metabolites in urine, plasma, and meconium by GC-MS using an immunoaffinity extraction procedure," Journal of Analytical Toxicology, vol. 24, Sep. 2000.

Fraser, A.D. et al., "Monitoring urinary excretion of cannabinoids by fluorescence-polarization immunoassay: a cannabiniod-to-creatinine ratio study," Ther Drug Monit. Dec. 2002;24(6):746-50, PubMed abstract 12451292.

Fraser, A.D. et al., "Urinary excretion profiles of 11-nor9-carboxy-delta9-tetrahydrocannabinol and 11-hydroxy-delta9-THC: cannabinoid metabolites to creatinine ratio study IV," Forensic Sci Int. Jul. 16, 2004;143(2-3):147-52, PubMed abstract 15240035.

Fraser, A.D. et al., "Urinary excretion profiles of 11-nor-9-carboxy-Delta9-tetrahydrocannabinol. Study III. A Delta9-THC-COOH to creatinine ratio study," Forensic Sci Int. Nov. 26, 2003;137(2-3):196-202, PubMed abstract 14609657.

Garrett, E.R. et al., "Pharmacokinetics of delta9-tetrahydrocannabinol in dogs," J Pharm Sci. Mar. 1977;66(3):395-407, PubMed abstract 845807.

Garrett, Edward R. et al., "Physicochemical properties, solubility, and protein binding of Delta9-tetrahydrocannabinol," J Pharm Sci. Jul. 1974;63(7):1056-64, abstract.

Gjerde, Hallvard et al., "Comparison of drug concentrations in blood and oral fluid collected with the Intercept® sampling device," Journal of Analytical Toxicology, vol. 34, May 2010.

Gjerde, H. et al., "Incidence of alcohol and drugs in fatally injured car drivers in Norway," Accid Anal Prev. Aug. 1993;25(4):479-83, PubMed abstract 8357462.

Goodwin, R.S. et al., "Delta(9)-tetrahydrocannabinol, 11-hydroxy-delta(9)-tetrahydrocannabinol and 11-nor-9-carboxy-delta(9)-tetrahydrocannabinol in human plasma after controlled oral administration of cannabinoids," Ther Drug Monit. Aug. 2006;28(4):545-51, PubMed abstract 16885723.

Green, Mitchell D. et al., "Glucuronidation of opioids, carboxylic acid-containing drugs, and hydroxylated xenobiotics catalyzed by expressed monkey UDP-glucuronosyltransferase 2B9 protein," Drug Metabolism and Disposition, vol. 25, No. 12, (1997).

Gross, Stanley J. et al., "Detection of recent cannabis use by saliva Delta9-THC radioimmunoassay," Journal of Analytical Toxicology, vol. 9, Jan./Feb. 1985.

Grotenhermen, F., "Pharmacokinetics and pharmacodynamics of cannabinids," Clin Pharmacokinet. 2003;42(4):327-60, PubMed abstract 12648025.

Gustafson, Richard A. et al., "Urinary cannabinoid detection times after controlled oral administration of Delta9-tetrahydrocannabinol to humans," Clinical Chemistry 49:7, 1114-1124 (2003).

Gustafson, Richard A. et al., "Urinary pharmacokinetics of 11-Nor-9-carboxy-delta9-tetrahydrocannabinol after controlled oral delat9-tetrahydrocannabinol administration," Journal of Analytical Toxicology, vol. 28, Apr. 2004.

Gustafson, R.A. et al., "Validated method for the simultaneous determination of Delta 9-tetrahydrocannabinol (THC), 11-hydroxy-THC and 11-nor-9-carboxy-THC in human plasma using solid phase extraction and gas chromatography-mass spectrometry with positive chemical ionization," J. Chromatogr B Analyt Technol Biomed Life Sci, Dec. 5, 2003;798(1):145-54, PubMed abstract 14630369.

Guy, G.W. et al., "A phase I, double blind, three-way crossover study to assess the pharmacokinetic profile of cannabis based medicine extract (CBME) administered sublingually in variant cannabinoid ratios in normal healthy male volunteers (GWPK0215)," Journal of Cannabis Therapeutics, vol. 3, No. 4, 2003, pp. 121-152.

Hall, B.J. et al., "Determination of cannabinoids in water and human saliva by solid-phase microextraction and quadrupole ion trap gas chromatography/mass spectrometry," Anal chem. May 1, 1998;70(9):1788-96, PubMed abstract 9599579.

Halldin, M.M. et al., "Identification of in vitro metabolites of delta 1-tetrahydrocannabinol formed by human livers," Drug Metab Dispos. Jul.-Aug. 1982;10(4):297-301, PubMed abstract 6126323.

Hampson, A.J. et al., "Cannabidiol and (−)delta9-tetrahydrocannabinol are neuroprotective antioxidants," Proc Natl Acad Sci U.S.A. Jul. 7, 1998; 95(14): 8268-8273.

Hanson, V.W. et al., "Comparison of 3H- and 125I-radioimmunoassay and gas chromatography/mass spectrometry for the determination of delta9-tetrahydrocannabinol and cannabinoids in blood and serum," Journal of Analytical Toxicology, vol. 7, Mar./Apr. 1983.

Harder, S. et al., "Concentration-effect relationship of delta-9-tetrahydrocannabiol and prediction of psychotropic effects after smoking marijuana," Int J Clin Pharmacol Ther. Apr. 1997;35(4):155-9, PubMed abstract 9112136.

Harvey, D.J. et al., "Metabolites of cannabidiol identified in human urine," Xenobiotic, Mar. 1990;20(3):303-20, PubMed abstract 2336840.

Hawks, Richard L., "The Analysis of Cannabinoids in Biological Fluids," NIDA Research Monograph 42, 1982.

Hazekamp, Arno et al., "Cannabis; extracting the medicine," thesis/dissertation 2007.

"Information for health care professionals: cannabis (marihuana, marijuana) and the cannabinoids," Health Canada, Feb. 2013.

Heishman, Stephen J. et al., "Effects of tetrahydrocannabinol content on marijuana smoking behavior, subjective reports, and performance," Pharmacology Biochemistry and Behavior, vol. 34, Issue 1, Sep. 1989, pp. 173-179, abstract.

Himes, Sarah K. et al., "Cannabinoids in exhaled breath following controlled administration of smoked cannabis," Clinical chemistry 59:12 1780-1789 (2013).

Huang, Wei et al., "Simultaneous determination of delta9-tetrahydrocannabinol and 11-nor-9-carboxy-delta9-tetrahydrocannabinol in human plasma by solid-phase extraction and gas chromatography-negative ion chemical ionization-mass spectrometry," Journal of Analytical Toxicology, vol. 25, Oct. 2001.

Huestis, Marilyn A. et al., "Blood cannabinoids. I. Absorption of THC and formation of 11-OH-THC and THCCOOH during and after smoking marijuana," Journal of Analytical Toxicology, vol. 16, Sep./Oct. 1992.

Huestis, Marilyn A. et al., "Blood cannabinoids. II. Models for the prediction of time of marijuana exposure from plasma concentraitons of delta9-tetrahydrocannabinol (THC) and 11-nor-9-carboxy-delta9-tetrahydrocannabinol (THCCOOH)," Journal of Analytical Toxicology, vol. 16, Sep./Oct. 1992.

Huestis, Marilyn A. et al., "Cannabinoid concentrations in hair from documented cannabis users," Forensic Sci Int. Jul. 4, 2007; 169(2-3): 129-136.

Huestis, Marilyn A. et al., "Alternative testing matrices," chapter 11 of the Drug Abuse Handbook, 1998 CRC Press LLC, ISBN 0-8493-2637-0.

Huestis, M.A. et al., "Characterization of the absorption phase of marijuana smoking," Clin Pharmacol Ther. Jul. 1992;52(1):31-41, PubMed abstract 1320536.

Huestis, Marilyn A. et al., "Detection times of marijuana metabolites in urine by immunoassay and GC-MS," Journal of Analytical Toxicology, vol. 19, Oct. 1995.

Huestis, Marilyn A. et al., "Differentiating new marijuana use from residual drug excretion in occasional marijuana users," Journal of Analytical Toxicology, vol. 22, Oct. 1998.

Huestis, Marilyn A. et al., "Estimating the time of last cannabis use from plasma delta9-tetrahydrocannabinol and 11-nor-9-carboxy-delta9-tetrahydrocannabinol concentrations," Clinical Chemistry 51:12 2289-2295 (2005).

Huestis, Marilyn A., "Human cannabinoid pharmacokinetics," Chem Biodivers. Aug. 2007; 4(8): 1770-1804.

Huestis, Marilyn A. et al., "Relationship of delta9-tetrahydrocannabinol concentrations in oral fluid and plasma after controlled administration of smoked cannabis," Journal of Analytical Toxicology, vol. 28, Sep. 2004.

(56) References Cited

OTHER PUBLICATIONS

Huestis, Marilyn A. et al., "Urinary excretion profiles of 11-nor-9-carboxy-delta9-tetrahydrocannabinol in humans after single smoked doses of marijuana," Journal of Analytical Toxicology, vol. 20, Oct. 1996.

Hunt, C.A. et al., "Evidence that cannabidiol does not significantly alter the pharmacokinetics of tetrahydrocannabinol in man," J Pharmacokinet Biopharm. Jun. 1981;9(3):245-60, PubMed abstract 6270295.

Hunt, C.A. et al., "Tolerance and disposition of tetrahydrocannabinol in man," J Pharmacol Exp Ther. Oct. 1980;215(1):35-44, PubMed abstract 6256518.

Iribarne, C. et al., "Involvement of cytochrome P450 3A4 enzyme in the N-demethylation of methadone in human liver microsomes," Chem Res Toxicol. Mar. 1996;9(2):365-73, PubMed abstract 8839037.

Jehanli, A. et al., "Blind trials of an onsite saliva drug test for marijuana and opiates," J Forensic Sci. Sep. 2001;46(5):1214-20, PubMed 11569567.

Joern, William A., "Surface adsorption of the urinary marijuana carboxy metabolite: the problem and a partial solution," Letter to the Editor, Journal of Analytical Toxicology, vol. 16, Nov./Dec. 1992.

Johansson, E. et al., "Determination of delta 1-tetrahydrocannabinol in human fat biopsies from marihuana users by gas chromatography-mass spectrometry," Biomed Chromatogr. Jan. 1989;3(1):35-8, PubMed abstract 2539872.

Johansson, E. et al., "Prolonged apparent half-life of delta 1-tetrahydrocannabinol in plasma of chronic marijuana users," J Pharm Pharmacol. May 1988;40(5):374-5, PubMed abstract 2899638.

Johannson, E. et al., "Terminal elimination plasma half-life of delta 1—tetrahydrocannabinol (delta 1-THC) in heavy users of marijuana," Eur J Clin Pharmacol. 1989;37(3):273-7, PubMed abstract 2558889.

Johansson, Eva et al., "Urinary excretion half-life of deltal-tetrahydrocannabinol-7-oic acid in heavy marijuana users after smoking," Journal of Analytical Toxicology, vol. 13, Jul./Aug. 1989.

Kadehijian, Leo, "Syva has been a leading developer and manufacturer of drugs-of-abuse tests for more than 30 years," Cannabinoid Issues: Passive inhalation, excretion patterns, and retention times, test result interpretation, Siemens Healthcare Diagnostics Inc., 2009.

Karst, Matthias et al., "Analgesic effect of the synthetic cannabinoid CT-3 on chronic neuropathic pain," JAMA. 2003;290(13):1757-1762.

Kelly, Peggy et al., "Metabolism of tetrahydrocannabinol in frequent and infrequent marijuana users," Journal of Analytical Toxicology, vol. 16, Jul./Aug. 1992.

Kemp, Philip M. et al., "Cannabinoids in Humans. II. The influence of three methods of hydrolysis on the concentration of THC and two metabolites in urine," Journal of Analytical Toxicology, vol. 19, Sep. 1995.

Kemp, Philip M. et al., "Cannabinoids in Humans. I. Analysis of delta9-tetrahydrocannabinol and six metabolites in plasma and urine using GC-MS," Journal of Analytical Toxicology, vol. 19, Sep. 1995.

Kidwell, David A. et al., "Testing for drugs of abuse in saliva and sweat," Journal of Chromatography B: Biomedical Sciences and Applications, vol. 713, Issue 1, Aug. 21, 1998, pp. 111-135, abstract.

Kintz, Pascal et al., "Detection of cannabis in oral fluid (saliva) and forehead wipes (sweat) from impaired drivers," Journal of Analytical Toxicology, vol. 24, Oct. 2000.

Kintz, Pascal et al., "Sweat testing for heroin and metabolites in a heroin maintenance program, " Clinical Chemistry 43:5, 736-739 (1997).

Kintz, P. et al., "Testing human hair for cannabis. II. Identification of TCD-COOH by GC-MS-NCI as a unique proof," J Forensic Sci. Jul. 1995;40(4):619-22, PubMed abstract 7595299.

Kovatsi, Leda et al., "Development and validation of a high-performance liquid chromatography method for the evaluation of niflumic acid cross-reactivity of two commercial immunoassays for cannabinoids in urine," Journal of Analytical Toxicology, vol. 34, May 2010.

Kreuz, D.S. et al., "Delta-9-tetrahydrocannabinol: localization in body fat," Science, Jan. 26, 1973;179(4071):391-3, PubMed abstract 4682965.

Krishna, D.R. et al., "Extrahepatic metabolism of drugs in humans," Clin Pharmacokinet. Feb. 1994;26(2):144-60, PubMed abstract 8162658.

Lafolie, P. et al., "Importance of creatinine analyses of urine when screening for abused drugs," Clin. Chem. 37/11, 1927-1931 (1991).

Laloup, M. et al., "Correlation of delta9-tetrahydrocannabinol concentrations determined by LC-MS-MS in oral fluid and plasma from impaired drivers and evaluation of the on-site Drager Drug Test," Forensic Sci Int. Sep. 12, 2006;161(2-3):175-9, PubMed abstract 16842950.

Law, B. et al., "Forensic aspects of the metabolism and excretion of cannabinoids following oral ingestion of cannabis resin," J Pharm Pharmacol. May 1984;36(5):289-94, PubMed abstract 6145762.

Lee, Sooyeun et al., "Estimation of the measurement uncertainty by the bottom-up approach for the determination of methamphetamine and amphetamine in urine," Journal of Analytical Toxicology, vol. 34, May 2010.

Lemberger, L. et al., "11-hydroxy-9-tetrahydrocannabinol: pharmacology, disposition, and metabolism of a major metabolite of marihuana in man," Science. Jul. 7, 1972;177(4043):62-4, PubMed abstract 5041775.

Lemberger, L. et al., "Delta-9-tetrahydrocannabinol: metabolism and disposition in long-term marihuana smokers," Science. Jul. 2, 1971;173(3991):72-4, PubMed abstract 5087483.

Lemberger, L. et al., "Marihuana: studies on the disposition and metabolism of delta-9-tetrahydrocannabinol in man," Science. Dec. 18, 1970;170(3964):1320-2, PubMed abstract 5479011.

Lindgren, J.E. et al., "Clinical effects and plasma levels of delta 9-tetrahydrocannabinol (delta 9-THC) in heavy and light users of cannabis," Psychopharmacology (Berl). 1981;74(3):208-12, PubMed 6267648.

Malfait, A.M. "The nonpsychoactive arthritic therapeutic cannabidiol is an oral anti-arthritic therapeutic in murine collagen-induced arthritis," Proc Natl Acad Sci USA Aug. 15, 2000;97(17):9561-9566.

Manno, Joseph E. et al., "Temporal indication of marijuana use can be estimated from plasma and urine concentrations of delta9-tetrahydrocannabinol, 11-hydroxy-delta9-tetrahydrocannabinol, and 11-nor-delta9-tetrahydrocannabinol-9-carboxylic acid," Journal of Analytical Toxicology, vol. 25, Oct. 2001.

Manolis, Antony et al., "The detection of delta9-tetrahydrocannabinol in the breath of human subjects," Clinical Biochem. 16,229 (1983).

"Marihuana '84," Proceedings of the Oxford Symposium on Cannabis, D.J. Harvy, editor, IRL Press, Oxford 1984.

Martin, B.R. et al., "3H-delta9-tetrahydrocannabinol distribution in pregnant dogs and their fetuses," Res Commun Chem Pathol Pharmacol. Jul. 1977;17(3):457-70, PubMed abstract 897339.

Mason, A.P. et al., "Cannabis: pharmacology and interpretation of effects," J Forensic Sci. Jul. 1985;30(3):615-31, PubMed abstract 2993473.

Mason, A.P. et al., "Ethanol, marijuana, and other drug use in 600 drivers killed in single-vehicle crashes in North Carolina, 1978-1981," J Forensic Sci. Oct. 1984;29(4):987-1026, PubMed abstract 6502125.

Matsunaga, T. et al., "Metabolism of delta 9-tetrahydrocannabinol by cytochrome P450 isozymes purified from hepatic microsomes of monkeys," Life Sci. 1995;56(23-24):2089-95, PubMed abstract 7776836.

Mattes, R.D. et al., "Bypassing the first-pass effect for the therapeutic use of cannabinoids," Pharmacol Biochem Behav. Mar. 1993;44(3):745-7, PubMed abstract 8383856.

Mattes, R.D. et al., "Cannabinoids and appetite stimulation," Pharmacol Biochem Behav. Sep. 1994;49(1):187-95, PubMed abstract 7816872.

(56) References Cited

OTHER PUBLICATIONS

McBurney, L.J. et al., "GC/MS and EMIT analyses for delta9-tetrahydrocannabinol metabolites in plasma and urine of human subjects," Journal of Analytical Toxicology, vol. 10, Mar./Apr. 1986.
Mechoulam, Raphael et al., "Cannabidiol: an overview of some chemical and pharmacological aspects. Part I: chemical aspects," Chemistry and Physics of Lipids 121 (2002) 35-43.
Mechoulam, Raphael, "Plant cannabinoids: a neglected pharmacological treasure trove," Br J Pharmacol. Dec. 2005; 146(7): 913-915.
Meier, H. et al., "Cannabis poisoning after eating salad," Schweiz Med Wochenschr. Feb. 8, 1997;127(6):214-8, PubMed abstract 9157527.
Menkes, D.B. et al., "Salivary THC following cannabis smoking correlates with subjective intoxication and heart rate," Psychopharmacology (Berl). 1991;103(2):277-9, PubMed abstract 1851311.
Mijuriya, Tod H., "Cannabis as a substitute for alcohol: a harm-reduction approach," Journal of Cannabis Therapeutics, vol. 4(1) 2004.
Milman, Garry et al., "Simultaneous quantification of cannabinoids and metabolites in oral fluid by two-dimensional gas chromatography mass spectrometry," J Chromatogr A. Feb. 26, 2010; 1217(9): 1513-1521.
Moeller, M.R. et al., "Simultaneous quantitation of delta-9-tetrahydrocannabinol (THC) and 11-nor-9-carboxy-delta-9-tetrahydrocannabinol (THC-COOH) in serum by GC/MS using deuterated internal standards and its application to a smoking study and forensic cases," J Forensic Sci. Jul. 1992;37(4):969-83, PubMed abstract 1324293.
Moldoveanu, Serban C. et al., "Differences in the chemical composition of the particulate phase of inhaled and exhaled cigarette mainstream smoke," Contributions to Tobacco Research 22(4), 290 (2007).
Moore, Christine et al., "Analytical procedure for the determination of the marijuana metabolite 11-nor-delta9-tetrahydrocannabinol-9-carboxylic acid in oral fluid specimens," Journal of Analytical Toxicology, vol. 30, Sep. 2006.
Moore, Christine et al., "Application of two-dimensional gas chromatography with electron capture chemical ionization mass spectrometry to the detection of 11-nor-delta9-tetrahydrocannabinol-9-carboxylic acid (THC-COOH) in hair," Journal of Analytical Toxicology, vol. 30, Apr. 2006.
Moore, Christine et al., "Detection of the marijuana metabolite 11-nor-delta9-tetrahydrocannabinol-9-carboxylic acid in oral fluid specimens and its contribution to positive results in screening assays," Journal of Analytical Toxicology, vol. 30, Sep. 2006.
Moore, Christine et al., "The determination of 11-nor-delta9-tetrahydrocannabinol-9-carboxylic acid (THC-COOH) in hair using negative ion gas chromatography-mass spectrometry and high-volume injection," Journal of Analytical Toxicology, vol. 25, Oct. 2001.
Morland, J. et al., "Cannabinoids in blood and urine after passive inhalation of cannabis smoke," J Forensic Sci. Oct. 1985;30(4):997-1002, PubMed abstract 2999292.
Mule, S.J. et al., "Active and realistic passive marijuana exposure tested by three immunoassays and GC/MS in urine," Journal of Analytical Toxicology, vol. 12, May/Jun. 1988.
Mura, P. et al., "Evaluation of six rapid tests for screening of cannabis in sweat, saliva and tears," Acta Clin Belg. 1999;53 Suppl 1:35-8, PubMed abstract 10216980.
Mura, P. et al., "THC can be detected in brain while absent in blood," Letter to the Editor, Journal of Analytical Toxicology, vol. 29, Nov./Dec. 2005.
Nadulski T. et al., "Randomized, double-blind, placebo-controlled study about the effects of cannabidiol (CBD) on the pharmacokinetics of Delat9-tetrahydrocannabinol (THC) after oral application of THC verses standardized cannabis extract," Ther Drug Monit. Dec. 2005;27(6):799-810.
Nadulski T. et al., "Simultaneous and sensitive analysis of THC, 11-OH-THC, THC-COOH, CBD, and CBN by GC-MS in plasma after oral application of small doses of THC and cannabis extract," Journal of Analytical Toxicology, vol. 29, Nov./Dec. 2005.
Nahas, Gabriel G. et al., "Pharmacokinetics of THC in brain and testis, male gametotoxicity and premature apoptosis of spermatozoa," Human Psycopharmacology: Clinical and Experimental, vol. 17, Issue 2, pp. 103-113, Mar. 2002, abstract.
Niedbala, R. Sam et al., "Detection of marijuana use by oral fluid and urine analysis following single-dose administration of smoked and oral marijuana, " Journal of Analytical Toxicology, vol. 25, Jul./Aug. 2001.
Niedbala, R. Sam et al., "Passive cannabis smoke exposure and oral fluid testing. II. Two studies of extreme cannabis smoke exposure in a motor vehicle," Journal of Analytical Toxicology, vol. 29, Oct. 2005.
Ohlsson, A. et al., "Plasma delta-9 tetrahydrocannabinol concentrations and clinical effects after oral and intravenous administration and smoking," Clin Pharmacol Ther. Sep. 1980;28(3):409-16, PubMed abstract 6250760.
Ohlsson, Agneta et al., "Single dose kinetics of deuterium labelled delta1-tetrahydrocnnabinol in heavy and light cannabis users," Biological Mass Spectrometry, vol. 9, Issue 1, pp. 6-10, Jan. 1982, abstract.
Owens, S. Michael et al., I Radioimmunoassay of delta-9-tetrahydrocannabinol in blood and plasma with a solid-phase second-antibody separation method, Clin. Chem. 27/4, 619-624 (1981).
Peel, H.W. et al., "Detection of drugs in saliva of impaired drivers," J Forensic Sci. Jan. 1984;29(1):185-9, PubMed abstract 6366113.
Perez-Reyes, M. et al., "The clinical pharmacology and dynamics of marihuana cigarette smoking," J Clin Pharmacol. Aug.-Sep. 1981;21(8-9 Suppl):201S-207S, PubMed abstract 6271825.
Perez-Reyes, M. et al., "Comparison of effects of marihuana cigarettes to three different potencies," Clin Pharmacol Ther. May 1982;31(5):617-24, PubMed abstract 6280918.
Perez-Reyes, M. et al., "Intravenous injection in man of 9-tetrahydrocannabinol and 11-OH-9-tetrahydrocannabinol," Science. Aug. 18, 1972;177(4049):633-5, PubMed abstract 4558903.
Perez-Reyes, Mario, "Marijuana smoking: factors that influence the bioavailability of tetrahydrocannabinol," NIDA Monograph 1990;99:42.
Piao, Wen et al., "Development of azo-based fluorescent probes to detect different levels of hypoxia," Angew. Chem. Int. Ed. 2013, 52, 13028-13032.
Quintela, Oscar et al., "Recovery of drugs of abuse from the immunalysis quantisal™ oral fluid collection device," Journal of Analytical Toxicology, vol. 30, Oct. 2006.
Rahim S.A. et al., "Colorimetric determination of ethanol in the presence of methanol and other species in aqueous solution," Talanta. Nov. 1992;39(11):1489-91, PubMed abstract 18965558.
Rohrich, J. et al., "Concentrations of delta9-tetrahydrocannabinol and 11-nor-9-carboxytetrahydrocannabinol in blood and urine after passive exposure to cannabis smoke in a coffee shop," Journal of Analytical Toxicology, vol. 34, May 2010.
Russo, E. et al., "A tale of two cannabinoids: the therapeutic rational for combining tetrahydrocannabinol and cannabidiol," Med Hypotheses. 2006;66(2):234-46, PubMed abstract 16209908.
Samyn N. et al., "On-site testing of saliva and sweat with Drugwipe and determination of concentrations of drugs of abuse in saliva, plasma and urine of suspected users," Int J Legal Med. 2000;113(3):150-4, PubMed abstract 10876986.
Scheuplein, Robert J., "Mechanism of percutaneous absorption. II. Transient diffusion and the relative importance of various routes of skin penetration," J. Invest. Dermatol 1967;48:79.
Schwartz, Richard H. et al., "Laboratory detection of marijuana use, Experience with a photometric immunoassay to measure urinary cannabinoids," Aj J Dis Child. 1985;139(11):1093-1096, abstract.
Schwilke, Eugene W. et al., "Delta9-tetrahydrocannabinol (THC), 11-hydroxy-THC, and 11-nor-9-carboxy-THC plasma pharmacokinetics during and after continuous high-dose oral THC," Clinical Chemistry 55:12 2180-2189 (2009).

(56) References Cited

OTHER PUBLICATIONS

Shaw, Leslie M. et al., "Ultrasensitive measurement of delta-9-tetrahydrocannabinol with a high energy dynode detector and electron-capture negative chemical-ionization mass spectrometry," Clin. Chem. 37/12, 2062-2068 (1991).

Skopp, G. et al., "Partition coefficient, blood to plasma ratio, protein binding and short-term stability of 11-nor-Delta(9)-carboxy tetrahydrocannabinol glucuronide," Forensic Sci Int. Mar. 28, 2002;126(1):17-23, PubMed abstract 11955826.

Soares, J.R. et al., "Significant developments in radioimmune methods applied to delta9-THC and its 9-substituted metabolites," Analysis of Cannabinoids Research Monograph 42, NIDA 1982.

Stinchcomb, A.L. et al., "Human skin permeation of Delta8-tetrahydrocannabinol, cannabidiol and cannbinol," J Pharm Pharmacol. Mar. 2004;56(3):291-7, PubMed abstract 15025853.

Strano-Rossi, Sabina et al., "Analysis of stimulants in oral fluid and urine by gas chromatography-mass spectrometry II: Pseudophedrine," Journal of Analytical Toxicology, vol. 34, May 2010.

Tan, Chongxiao et al., "Direct detection of delta9-tetrahydrocannabinol in aqueous samples using a homogeneous increasing fluorescence immunoassay (HiFi)," Anal Bioaanal Chem, 2010. 8 pgs.

Teshima, N. et al, "Determination of acetone in breath", Analytica Chimica Acta, 2005, 535, pp. 189-199.

Toennes, Stefan W. et al., "Pharmacokinetic properties of delta9-tetrahydrocannabinol in oral fluid of occasional and chronic users," Journal of Analytical Toxicology, vol. 34, May 2010.

Turner, Carton E. et al., "Constituents of cannabis sativa 1. XVII. A review of the natural constituents," J. Nat. Prod. 1980;43:169.

Valiveti, S. et al., "In vitro/in vivo correlation studies for transdermal delta 8-THC development," J Pharm Sci. May 2004;93(5):1154-64, PubMed abstract 15067692.

Van der Kooy, F. et al., "Cannabis smoke condensate I: The effect of different preparation methods on tetrahydrocannabinol levels," Inhalation Toxicology, 20:801-804, 2008.

Vinciguerra, V. et al., "Inhalation marijuana as an antiemetic for cancer chemotherapy," NY State J Med. Oct. 1988;88(10):525-7.

Wall, M.E. et al., "The metabolism of delta 9-tetrahydrocannabinol and related cannabinoids in man," J Clin Pharmacol. Aug.-Sep. 1981;21 (8-9 Suppl):178S-189S, PubMed abstract 6271823.

Wall, M.E. et al., "Metabolism, disposition, and kinetics of delta-9-tetrahydrocannabinol in men and women," Clin Pharmacol Ther. Sep. 1983;34(3):352-63, PubMed abstract 6309462.

Walsh, J. Michael et al., "An evaluation of rapid point-of-collection oral fluid drug-testing devices," Journal of Analytical Toxicology, vol. 27, Oct. 2003.

Watanabe, K. et al., "Brain microsomal oxidation of delta 8- and delta 9-tetrahydrocannabinol," Biochem Biophys Res Commun. Nov. 30, 1988;157(1):75-80, PubMed abstract 2848522.

Widman, M. et al., "Metabolism of delta 1-tetrahydrocannabinol by the isolated perfused dog lung. Comparison with in vitro liver matabolism." J Phar Pharmacol. Nov. 1975;27(11):842-8, PubMed abstract 1493.

Williams, P.L. et al., "Identification in human urine of delta 9-tetrahydrocannabinol-11-oic acid glucuronide: a tetrahydrocannabinol metabolite," J Pharm Pharmacol. Jul. 1980;32(7):445-8, PubMed abstract 6105177.

Wingert, William E., "Lowering cutoffs for initial and confirmation testing for cocaine and marijuana: large-scale study of effects on the rates of drug-positive results," Clinical Chemistry 43:1 100-103 (1997).

Zajicek, J. et al., "Cannabinoids for treatment of spasticity and other symptoms related to multiple sclerosis (CAMS study): multicentre randomised placebo-controlled trial," Lancet. Nov. 8, 2003;362(9395):1517-26, abstract.

Zias, Joe et al., "Early medical use of cannabis," Nature; May 20, 1993; 363,6426; Research Library Core p. 215.

Zuardi, A.W. et al., "Action of cannabidiol on the anxiety and other effects produced by delta 9-THC in normal subjects," Psychopharmacology (Berl). 1982;76(3):245-50, PubMed abstract 6285406.

U.S. Appl. No. 15/650,537, filed Jul. 14, 2017, Gordon et al.
U.S. Appl. No. 14/641,412, filed Mar. 8, 2015, Lynn et al.
U.S. Appl. No. 15/875,195, filed Jan. 19, 2018, Lynn et al.
U.S. Appl. No. 15/943,123, filed Apr. 2, 2018, Lynn et al.
U.S. Appl. No. 14/641,412, Office Action dated May 19, 2016.
U.S. Appl. No. 14/641,412, Final Office Action dated Dec. 5, 2016.
U.S. Appl. No. 14/641,412, Office Action dated Jun. 26, 2017.
U.S. Appl. No. 14/641,412, Notice of Allowance dated Jan. 9, 2018.
U.S. Appl. No. 14/641,412, Corrected Notice of Allowability dated Apr. 18, 2018.
U.S. Appl. No. 15/875,195, Office Action dated Apr. 19, 2018.

* cited by examiner

METHOD AND APPARATUS FOR DETECTING ACUTE USE OF TARGET SUBSTANCE(S)

CROSS-REFERENCE TO RELATED APPLICATIONS

The present application is a continuation of U.S. patent application Ser. No. 14/641,412, filed Mar. 8, 2015, and entitled "Method And Apparatus For Detecting Acute Use Of Target Substance(s)," which claims the benefit of U.S. Provisional Patent Application No. 61/950,173, filed Mar. 9, 2014, entitled "Method and Apparatus for Detecting Acute Use of Target Substance(s)", the disclosures of both of which are hereby incorporated herein by reference for all purposes.

BACKGROUND

It is well known that operating a vehicle under the influence of substances that impair operating conditions is dangerous. For example, dangers of driving a car under the influence of alcohol or drugs of abuse are established. With alcohol, existing breathanalyzer often used by law enforcement officers roadside can determine the level of alcohol in the driver's system at the time of administering the breathalyzer test. However, no such device exists in the market place that can detect and quantify tetrahydrocannabinol (THC) levels-the principal psychoactive constituent of cannabis-of suspected users operating a vehicle when pulled over by a law enforcement officer roadside.

With legalization of marijuana expanding and the risk of marijuana-associated impaired driving increasing, there is a need for a device that can quantify THC (and other substances of abuse) levels of suspected users roadside to establish recent or acute consumption or use of marijuana alone or in combination with other substances of abuse such as alcohol, codeine, cocaine, morphine, or methamphetamine.

SUMMARY

The purpose and advantages of the present disclosure will be set forth in and apparent from the description that follows, as well as will be learned by practice of the disclosure. Additional advantages of the present disclosure will be realized and attained by the methods and systems particularly pointed out in the written description and claims hereof, as well as from the appended drawings.

To achieve these and other advantages and in accordance with the purpose of the present disclosure, as embodied herein and broadly described, the present disclosure includes devices and methods for acute detection of target substance under analysis such that where acute detection of one or more target substances provide confirmation of recent use or ingestion of the target substance. For example, the detection devices of the various embodiments of the present disclosure provides confirmation of recent use or ingestion of one or more of cannabis, alcohol, codeine, cocaine, morphine, methamphetamine, or other substance of abuse. Embodiments of the present disclosure provide compact, handheld detection devices for use such as in road-side testing by law enforcement, testing in public and private locations such as schools (e.g., school dances), at home, or place of business, to determine whether a person or persons is under the influence of one or more of the target substances.

Accordingly, in certain embodiments, there is provided a method that includes performing acquisition of a sample having a plurality of analysis substances, executing, using one or more processors, a first substance detection routine and a second substance detection routine for detecting the presence of the first analysis substance and the second analysis substance in the acquired sample, respectively; and generating an output signal based on the executed first and second substance detection routines, wherein the output signal corresponds to the acute detection of target substance(s) in the sample.

A method in accordance with another embodiment includes performing acquisition of a sample having one or more analysis substances, executing, using one or more processors, a first substance detection routine and a second substance detection routine for detecting the presence of the first analysis substance and the second analysis substance in the acquired sample, respectively, generating an output signal based on the executed first and second substance detection routines, wherein the output signal corresponds to the presence in the sample of target substance associated with the one or more of the analysis substances, where the second substance detection routine is performed within a predetermined time period after the completion of the first substance detection routine, where the first analysis substance is the same as the second analysis substance, and further, where the output signal confirms the acute detection of the target substance in the acquired sample when a determined gradient corresponds to a predetermined gradient, where the gradient is determined based on the level of the detected first analysis substance and the detected second analysis substance.

A method in still a further embodiment includes performing acquisition of a sample having one or more analysis substances, executing, using one or more processors, a first substance detection routine for detecting the presence of the first analysis substance, a second substance detection routine for detecting the presence of the first analysis substance, and a third substance detection routine for detecting the presence of the second analysis substance, and generating an output signal based on the executed first, second and third substance detection routines, wherein the output signal corresponds to the presence in the sample of target substance associated with the one or more of the analysis substances, where the second substance detection routine is performed within a predetermined time period after the completion of the first substance detection routine and further where the output signal confirms acute detection of the target substance in the acquired sample when (1) a determined gradient of the first analysis substance corresponds to a predetermined gradient profile, where the gradient is determined based on the level of the detected first analysis substance from the first substance detection routine and the second substance detection routine, and (2) the presence of the second analysis substance associated with the target sample from the third substance detection routine is determined.

An apparatus in accordance with one embodiment includes one or more sampling modules configured to acquire one or more samples having one or more analysis substances, a processing unit operatively coupled to the one or more sampling modules configured to execute a first substance detection routine and a second substance detection routine for detecting the presence of the first analysis substance and the second analysis substance in the acquired one or more samples, respectively, and an output unit operatively coupled to the processing unit and configured to output one or more signals based on the executed first and second substance detection routines, wherein the output signal corresponds to acute detection of target substance in the one or more samples. In certain embodiments, the one or more sampling modules includes a single use replaceable cartridge that mate with the housing of the apparatus and is discarded after single use. More specifically, each cartridge in certain embodiments is used to acquire the sample (breath, saliva etc.), which is processed using one or more routines described herein to determine the level of target substance(s) (THC, alcohol, or both THC and alcohol) in the acquired sample.

An apparatus in accordance with still yet further embodiment includes one or more sampling modules configured to acquire one or more samples having one or more analysis substances, a processing unit operatively coupled to the one or more sampling modules configured to execute a first substance detection routine and a second substance detection routine for detecting the presence of the first analysis substance and the second analysis substance in the acquired sample, respectively to generate one or more signals based on the executed first and second substance detection routines, wherein the generated one or more signals corresponds to acute detection of target substance in the one or more samples, where the second substance detection routine is performed within a predetermined time period after the completion of the first substance detection routine, where the first analysis substance is the same as the second analysis substance, and further, where the one or more signals confirms the acute detection of the target substance in the acquired sample when a determined gradient corresponds to a predetermined gradient, where the gradient is determined based on the level of the detected first analysis substance and the detected second analysis substance.

An apparatus in yet still a further embodiment includes one or more sampling modules configured to acquire one or more samples having one or more analysis substances, a processing unit operatively coupled to the one or more sampling modules configured to execute a first substance detection routine for detecting the presence of the first analysis substance, a second substance detection routine for detecting the presence of the first analysis substance, and a third substance detection routine for detecting the presence of the second analysis substance, the processing unit further configured to generate an output signal based on the executed first, second and third substance detection routines, wherein the output signal corresponds to acute detection of target substance in the one or more samples, where the second substance detection routine is performed within a predetermined time period after the completion of the first substance detection routine, and further where the output signal confirms acute detection of the target substance in the acquired sample when (1) a determined gradient of the first analysis substance corresponds to a gradient profile, where the gradient is determined based on the level of the detected first analysis substance from the first substance detection routine and the second substance detection routine, and (2) the presence of the second analysis substance associated with the target sample from the third substance detection routine is determined.

It is to be understood that both the foregoing general description and the following detailed description are exemplary and are intended to provide further explanation of the disclosure claimed. The accompanying drawings are included to illustrate and provide a further understanding of the method and device of the disclosure. Together with the description, the drawings serve to explain the principles of the present disclosure.

DETAILED DESCRIPTION

Figure 1:
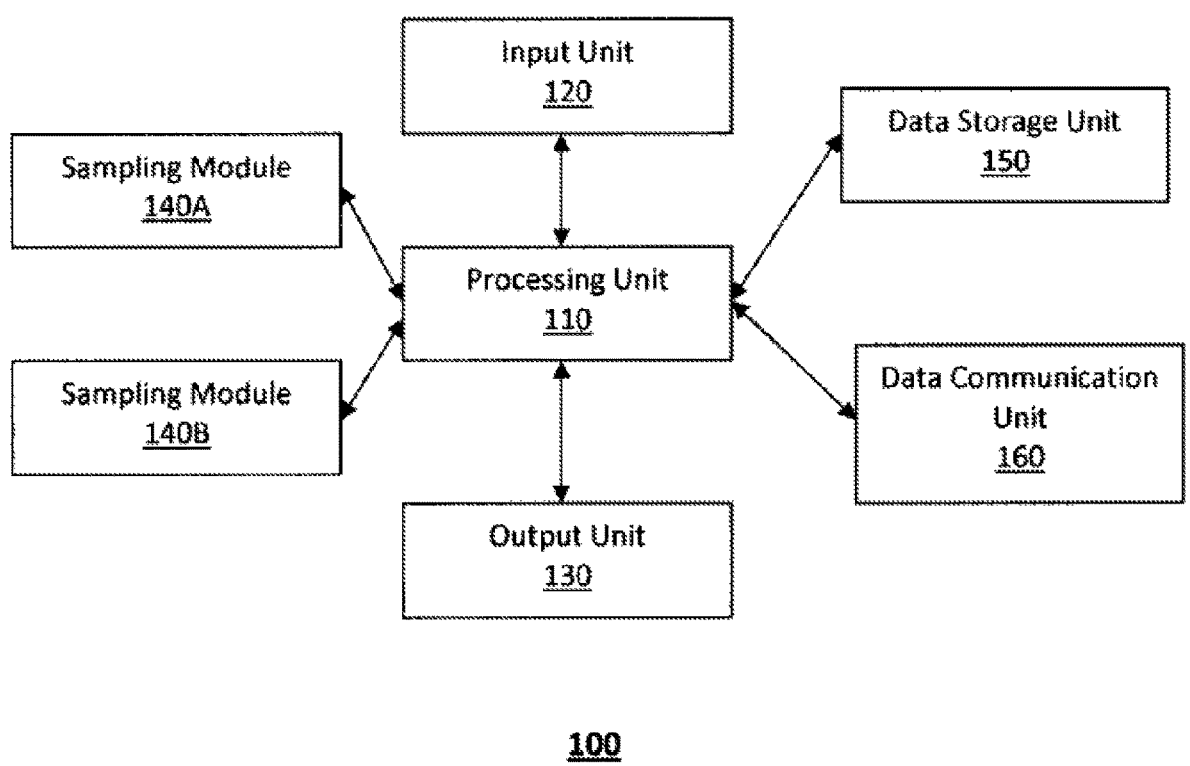
FIG. 1 illustrates a block diagram of the device for acute detection of target substance in accordance with one embodiment of the present disclosure.

As summarized above and as described in further detail below, in accordance with various embodiments of the present disclosure, there are provided methods, devices, systems and kits for acute detection of target substance in one or more samples including, for example, oral fluid sample and/or exhaled breath.

In certain embodiments, the detection device is configured to receive a first sample from a sample source of a person such as oral fluid or exhaled breath, and to analyze the received sample to determine presence of a first substance, and to receive a second sample from the same person, and to analyze the received second sample to determine the presence of a second substance. In certain embodiments, when the detection device determines that the first substance is present in the first sample, and further, the second substance is present in the second sample, the detection device generates an indication or a signal associated with the confirmation of target substance presence in the sample source of the person. In certain embodiments, the first and the second samples are different samples such as oral fluid and exhaled breath. In certain embodiments, the first and the second samples are the same type of samples such as oral fluid or exhaled breath.

In certain embodiments, the detection device is programmed to analyze the first sample and the second sample concurrently. In certain embodiments, the second sample is acquired or received a predetermined time period after the first sample is acquired or received. For example, the second sample may be received within 5 minutes of receiving the first sample. In other embodiments, the second sample may be received within 10 minutes, within 15 minutes, within 20 minutes, within 25 minutes, within 30 minutes or more after receiving the first sample. In certain embodiments, the detection device is programmed to analyze the second sample differently based on when the second sample is received relative to when the first sample is received, in order to determine the presence of the first or the second substance for acute detection of the target substance.

In certain embodiments, the detection device is configured to receive, process and analyze one or more samples received to determine a relative gradient in the level of substance detected in the one or more samples received, for acute detection of the target substance. For example, in certain embodiments, the detection device is configured to analyze the samples to determine the substance levels over a predetermined time period such as 15 minutes, 20 minutes, 25 minutes, 30 minutes, or greater than 30 minutes, for example, to identify the presence of a relative gradient or slope over the predetermined time period, to confirm acute presence of the target substance. In certain embodiments, the detection device, for a particular substance under detection, is programmed to confirm acute detection of the target substance when a positive gradient is determined over a specific time period. In other embodiments, the detection device is programmed to confirm acute detection of the target substance when a positive gradient is determined over a first time period, and a negative gradient is determined over a second time period. In certain embodiments, the first time period precedes the second time period. In certain embodiments, the first time period is shorter than the second time period.

In certain embodiments, the detection device uses different sampling techniques depending upon the type of sample received, such as one or more of mass spectrometry, gas chromatography mass spectrometry, high pressure mass spectrometry, liquid chromatography mass spectrometry, or two dimensional gas chromatography mass spectrometry, for example, as described in U.S. Pat. Nos. 7,790,400, 8,518,653, 8,525,111, US Patent Publication No. 2012/0302907, and US Patent Publication No. 2012/0302907, disclosures of each of which are incorporated by reference for all purposes.

FIG. 1 illustrates a block diagram of the device for acute detection of target substance in accordance with one embodiment of the present disclosure. Referring to FIG. 1, detection device 100 in certain embodiments includes a controller or processing unit 110 operatively coupled to data storage unit 150 and an input unit 120 and an output unit 130. In certain embodiments, processing unit 110 includes, but not limited to, one or more microprocessors, application specific integrated circuit (ASIC), single core processor, multi core processors, system on a chip (SoC) or any other data processing unit that is configured or programmed to execute one or more algorithms or programs to execute one or more functions. Referring back to FIG. 1, input unit 120 in certain embodiment includes one or more buttons, keyboards, keypads, touch-sensitive screen, pressure sensitive screen or any other input unit for inputting data or command for detection by the processing unit 110 for execution.

In certain embodiments, output unit 130 includes a visual display (for example, a screen, a touch sensitive screen, a color screen, a bit map screen or any other display component for displaying information), an audible output unit (for example, a speaker), a tactile output unit, or any other output component that is configured to output visual, tactile, audible, or a combination of such outputs, generated, for example, but the processing unit 110. Referring still to FIG. 1, data storage unit 150 in certain embodiments includes one or more of random access memory (RAM), read-only memory (ROM), electrically erasable programmable random access memory (EEPROM), flash memory, or any other types or variations of volatile memory or non-volatile memory.

In certain embodiments, detection device includes data communication unit 160 operatively coupled to the processing unit 110 for data communication. In certain embodiments, data communication unit 160 includes physical ports such as mini-USB ports, USB ports, RS-232 ports or any other wired connection ports to support data transfer or communication between the detection device and other device such as a personal computer, a mobile telephone, a tablet computing device, a server terminal, and/or with data network such as, for example, a public data network, a secured data network, a cloud data network, and the like. In other embodiments, the data communication unit 160 includes wireless data ports such as Bluetooth data ports, infrared data ports, RF communication ports, near field communication data ports, and the like. In certain embodiments, detection device does not include the data communication unit 160 and/or the analyzed data are stored in the data storage unit 150 of the detection device 100.

In certain embodiments, the detection device 100 is configured to communicate with the one or more other devices and/or one or more data networks for data transfer, device software upgrade, programming of detection device 100 (such as, for example, receiving or downloading pre-determined gradient profiles for target substances of interest for analysis by the detection device 100.

Referring back to FIG. 1, in certain embodiments, detection device 100 includes one or more sampling modules 140A, 140B. For example, in certain embodiments, detection device 100 includes one sampling module 140A. In other embodiments, detection device 100 includes two or more sampling modules 140A, 140B, etc. In such embodiments where multiple sampling modules 140A, 140B etc. are provided in the detection device 100, the processing unit 110 is configured to execute sampling algorithms to operate the sampling modules 140A, 140B, etc., such that each of the plurality of sampling modules 140A, 140B, etc. performs sampling routines that are the same or different sampling routines from each other.

In certain embodiments sampling modules 140A, 140B are single use replaceable cartridges that mate with the housing of the detection device 100 and are discarded or retained for evidentiary purposes after each use. The housing of the detection device 100 in certain embodiments is configured to releasably mate with the housing of the cartridge so that the cartridge can be easily and readily replaced after each use. Further, in certain embodiments, the single use cartridge includes an inlet such as an inlet vent that is configured to receive breath samples by having a person exhale into the inlet vent of the cartridge, and the cartridge retain the breath sample for analysis. In certain embodiments, the single use cartridge includes sample acquisition areas around or proximate to the inlet vent to acquire saliva sample when the person places his or her mouth around the inlet vent to exhale. In such configurations, both breath sample and saliva sample are acquired from the single use cartridge.

In certain embodiments, processing unit 110 is configured to detect the type of sample (oral fluid, exhaled breath etc.), and based on the detected sample type, retrieve the suitable sampling algorithm to operate the sampling modules. For example, in certain embodiments, sampling module 140A and sampling module 140B are configured to perform one of mass spectrometry, gas chromatography mass spectrometry, high pressure mass spectrometry, liquid chromatography mass spectrometry, or two-dimensional gas chromatography mass spectrometry on the received sample, under the control of the processing unit 110. In certain embodiments, the detection device includes multiple sampling modules 140A, 140B, both programmed to perform the same type of sampling procedure.

In this manner, in certain embodiments, detection device 100 is configured to receive one or more same or different type of samples, and perform analysis on the received one or more samples using the same or different sampling techniques to detect one or plural substances. Upon detection of the one or more substances, detection device 100 in certain embodiments is configured to generate an output signal (visual, audible, vibratory, or one or more combinations thereof), confirming acute detection of the target substance. In certain embodiments, target substance includes one or more of cannabis, alcohol, codeine, cocaine, morphine, methamphetamine, or other substance of abuse. In certain embodiments, substances for detection in the samples include one or more of cannabinoid including tetrahydrocannabinol (THC), cannabinol (CBN), 11-Hydroxy-$\Delta^9$-tetrahydrocannabinol (11OH-THC), 11-nor-9-Carboxy-THC (THC-COOH), alcohol, codeine, cocaine, morphine, methamphetamine, or other substance of abuse or its metabolites.

In certain embodiments, the processing unit 110 confirms the presence of detectable substances based on the sample analysis when a predetermined amount of the substance is detected in the sample, for example, in microgram, nanogram or picogram range or level. Upon detection confirmation of the detectable substance, in certain embodiments, processing unit 110 confirms acute presence of target substance. For example, in certain embodiments, the processing unit 110 of the detection device 100 is configured to provide a positive indication of acute detection of cannabis based on detection of one or more metabolites of cannabis such as 11-OH-THC or THC-COOH. In certain embodiments, processing unit 110 analyzes temporally spaced sample acquisition, and determines one or more gradients of the detectable substance level based on sample analysis, based upon which the processing unit confirms acute presence of target substance.

Figure 2:
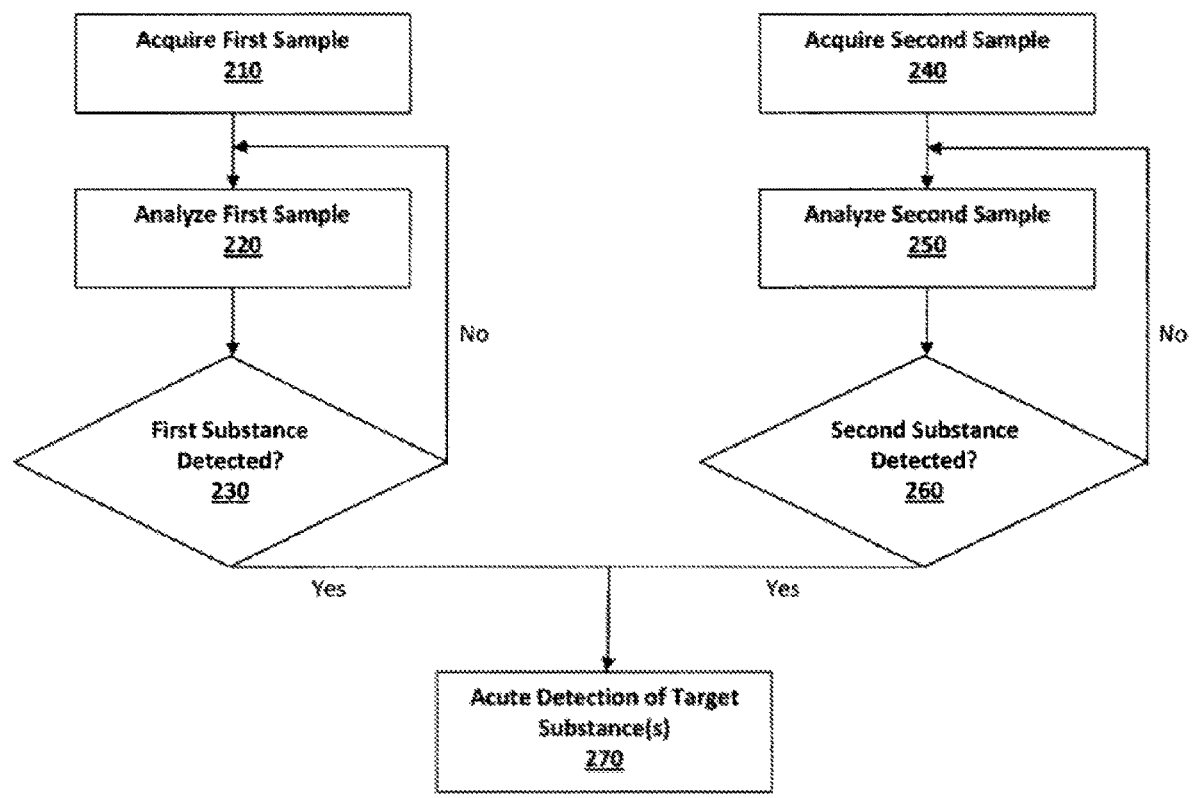
FIG. 2 is a flowchart illustrating acute detection algorithm executed by the device of FIG. 1 in accordance with one embodiment.

FIG. 2 is a flowchart illustrating acute detection algorithm executed by the device of FIG. 1 in accordance with one embodiment. Referring to FIG. 2, in certain embodiments, the first sample under analysis is acquired (210) by sampling module 140A and analyzed (220) by the processing unit 110 operatively coupled to the sampling module 140A. The processing unit 110 determines whether the first substance is detected in the first sample (230), and if not, the routine returns to analyze the first sample (220) again. Concurrent with the acquisition of the first sample (210), a second sample is acquired by sampling module 140B (240) and analyzed (250) by the processing unit 110 that is operatively coupled to the second sampling module 140B. The processing unit determines whether the second substance is detected in the second sample (260), and if not, the routine returns to analyze the second sample again (250).

Referring back to FIG. 2, when the processing unit 110 determines that the first substance is detected (230) and the second substance is detected (260), in certain embodiments, the processing unit 110 generates one or more signals indicating acute detection of target substance (270), and outputs an indication at the output unit (130) corresponding to the acute detection of the target substance. In certain embodiments, the second sample is acquired after the first sample, such that the processing unit 110 is configured to perform the acquisition (240), analysis (250) and detection of the second substance (260) in the first sample, after the processing unit 110 has performed acquisition (210), analysis (220) and detection of the first substance (230) in the first sample. In further embodiments, the source of the first sample and the second sample are the same such that the same or similar sampling techniques are used by the sampling module 140A and sampling module 140B under the control of the processing unit 110. Further, in still other embodiments, additional samples may be acquired, analyzed and processed for detection of additional substances.

In certain embodiments, the first and second substances are the same substances having the same or similar chemical composition or characteristics. In other embodiments, the first and second substances for detection may be related but different substances. For example, in certain embodiments, the first substance for detection is THC and the second substance for detection is a metabolite of THC such as, for example, 11-OH-THC. In certain embodiments, the first substance for detection is a first metabolite of THC such as, for example, THC-COOH, and the second substance for detection is a second metabolite of THC such as, for example, 11-OH-THC. In still further embodiments, the first substance for detection is THC and the second substance for detection is alcohol. In still further embodiments, the first substance for detection is THC and the second substance for detection is alcohol whereby the acute detection of target substance (270) includes detection of both cannabis and alcohol as target substances. In yet still further embodiments, the first substance for detection is THC and the second substance for detection is one or more of codeine, cocaine, morphine, methamphetamine, or other substance of abuse.

Figure 3:
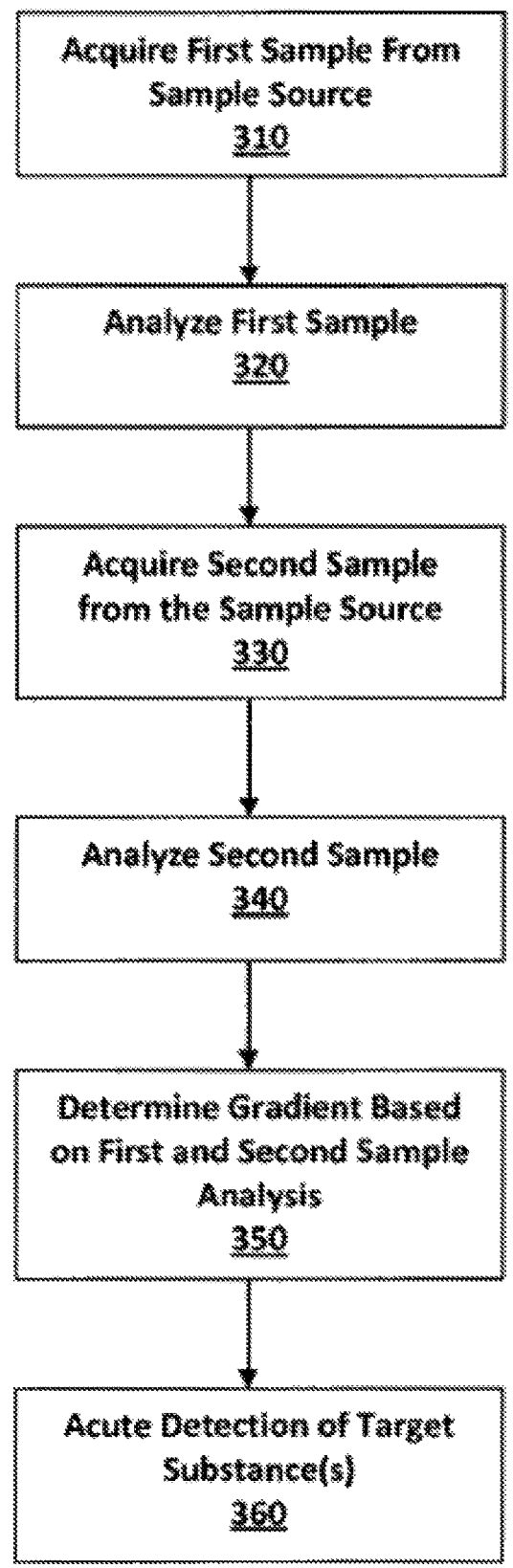
FIG. 3 is a flowchart illustrating acute detection algorithm executed by the device of FIG. 1 in accordance with another embodiment.

FIG. 3 is a flowchart illustrating acute detection algorithm executed by the device of FIG. 1 in accordance with another embodiment. Referring to FIG. 3, in certain embodiments, first sample for a sample source such as oral fluid or exhaled breath is acquired by sampling module 140A (310) and analyzed (320). After a predetermined time from the acquisition of the first sample (for example, after 5 minutes, or 10 minutes, or 15 minutes, or 20 minutes, 25 minutes or 30 minutes or greater), a second sample from the same sample source is acquired (330) and analyzed (340).

After analysis of the first and second samples, a gradient is determined in certain embodiments by the processing unit 110 based on the difference between the level of substance detected in the first sample and the level of substance detected in the second sample (350). When the determined gradient corresponds to a predetermined gradient profile, processing unit 110 is configured to generate one or more signals corresponding to acute detection of target substance (360). For example, in certain embodiments, the gradient profile includes a positive slope between the level of detected first substance and the level of detected second substance. In certain embodiments, the gradient profile includes a negative slope. Within the scope of the present disclosure, the gradient profile corresponding to the acute detection of target substance may vary depending upon the target substance for acute detection. In certain embodiments, one or more gradient profiles may be stored in the data storage unit 150 which is retrieved by the processing unit 110 for comparison with the generated or determined gradient based on the levels of first and second substances, and/or based on the half-life data or profile of the target substance and/or the first and second substances.

Figure 4:
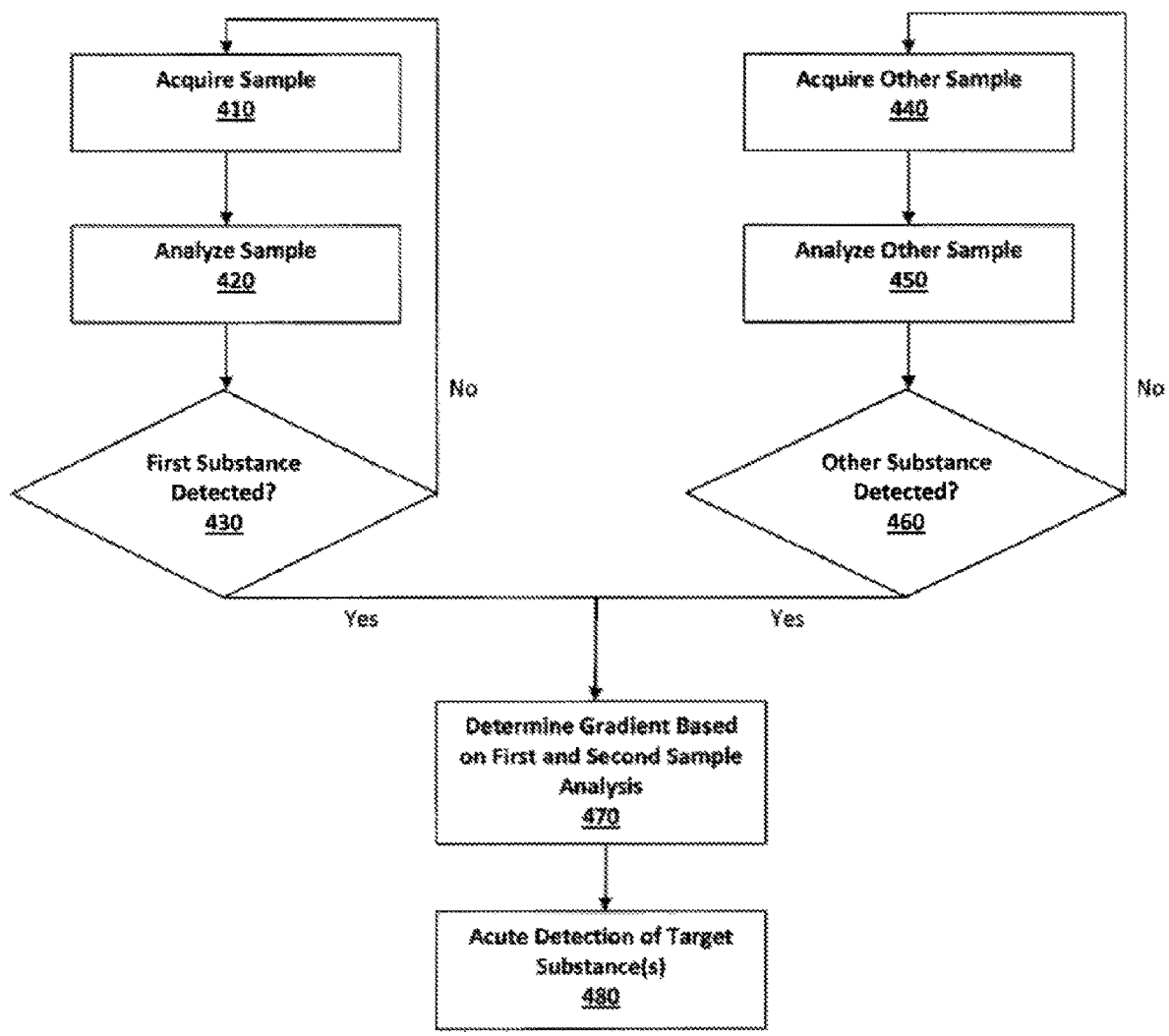
FIG. 4 is a flowchart illustrating acute detection algorithm executed by the device of FIG. 1 in accordance with another embodiment.

FIG. 4 is a flowchart illustrating acute detection algorithm executed by the device of FIG. 1 in accordance with another embodiment. Referring to FIG. 4, samples are acquired and analyzed for detection of the respective substances (410-460) similar to the corresponding routines discussed above in conjunction with steps 210-260 of FIG. 2. As discussed above, the sample acquisitions (410, 440) may be concurrently performed, or serially performed such that the one of the two samples is acquired after the other of the two samples. Referring back to FIG. 4, after the detection of the substances for analysis, the processing unit 110 determines a gradient based on the level of the detected substances. Similar to the gradient analysis discussed above in conjunction with FIG. 3, the processing unit 110 generates one or more signals indicating acute detection of the target substance when the determined one or more gradients correspond to or matches with the one or more gradient profiles for the substances under analysis.

Referring back to FIG. 4, in certain embodiments, detection device 100 is configured to acquire sample (410) under analysis by sampling module 140A and analyzed (420) by the processing unit 110 operatively coupled to the sampling module 140A. The processing unit 110 determines whether the substance is detected in the sample (430), and if not, the routine returns to analyze the sample (420) again. In certain embodiments, the processing unit 110 determines the presence and the level of the detected substance in the sample (430). After a predetermined amount of time from detection and determination of the level of the substance (430), the detection device 100 in certain embodiments performs sample acquisition (410), sample analysis (420) and substance detection (430) routines again to determine the level of the detected substance in another sample. In certain embodiments, processing unit 110 is configured to perform the sub-routines 410-430 two or more times to determine two or more levels of detected substance under analysis (470) which is used to determine a gradient based on the analysis of the samples. The determined gradient in certain embodiments is used for comparison to a predetermined gradient profile of the substance under analysis to confirm acute detection of target substance (480).

As discussed above, one or more of the sub-routines 410-430 may be repeated until the detection device 100 confirms the detection of the substance (430) to generate multiple levels of detected substance. Referring back to FIG. 4, in certain embodiments, another sample is acquired by sampling module 140B (440) and analyzed (450) by the processing unit 110 that is operatively coupled to the second sampling module 140B. The processing unit 110 determines whether the substance is detected in the other sample (460), and if not, the routine returns to analyze the other sample (450) again. In certain embodiments, the processing unit 110 determines the presence and the level of the detected substance in the other sample (460). After a predetermined amount of time from detection and determination of the level of the substance (460), the detection device 100 in certain embodiments performs sample acquisition (440) of the other sample, sample analysis (450) and substance detection (460) routines again to determine the level of the detected substance in the other sample. In certain embodiments, processing unit 110 is configured to perform the sub-routines 410-430 two or more times to determine two or more levels of detected substance under analysis (470) which is used to determine a gradient based on the analysis of the samples. The determined gradient in certain embodiments is used for comparison to a predetermined gradient profile of the substance under analysis to confirm acute detection of target substance (480).

In certain embodiments, the detection device 100 detects the presence and the levels of THC and the presence and the levels of its metabolite such as, for example, but not limited to, 11-OH-THC, and thereafter, performs the gradient analysis to confirm acute detection of cannabis in the samples providing a positive indication of cannabis use within a predetermined time from the sample acquisition (for example, within 1-2 hours before sample acquisition, less than an hour before sample acquisition, within 2-3 hours before sample acquisition, within 3-4 hours of sample acquisition, within 4-5 hours of sample acquisition, or within 8 hours of sample acquisition).

Accordingly, in certain embodiments, there is provided a method including performing acquisition of a sample having a plurality of analysis substances, executing, using one or more processors, a first substance detection routine and a second substance detection routine for detecting the presence of the first analysis substance and the second analysis substance in the acquired sample, respectively; and generating an output signal based on the executed first and second substance detection routines, wherein the output signal corresponds to the acute detection of target substance in the sample.

The sample in certain embodiments includes oral fluid sample.

The sample in certain embodiments includes exhaled breath sample.

The sample in certain embodiments includes a combination of oral fluid sample and exhaled breath sample.

In certain embodiments, the first substance detection routine and the second substance detection routine are performed simultaneously.

In certain embodiments, the first substance detection routine and the second substance detection routine are performed sequentially.

In certain embodiments, the target substance include cannabis.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample. Further, in certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the sample acquisition is performed using one or more of mass spectrometry, gas chromatography mass spectrometry, high pressure mass spectrometry, liquid chromatography mass spectrometry, or two dimensional gas chromatography mass spectrometry.

A method in accordance with another embodiment includes performing acquisition of a sample having one or more analysis substances, executing, using one or more processors, a first substance detection routine and a second substance detection routine for detecting the presence of the first analysis substance and the second analysis substance in the acquired sample, respectively, generating an output signal based on the executed first and second substance detection routines, wherein the output signal corresponds to the presence in the sample of target substance associated with the one or more of the analysis substances, where the second substance detection routine is performed within a predetermined time period after the completion of the first substance detection routine, where the first analysis substance is the same as the second analysis substance, and further, where the output signal confirms the acute detection of the target substance in the acquired sample when a determined gradient corresponds to a predetermined gradient, where the gradient is determined based on the level of the detected first analysis substance and the detected second analysis substance.

The sample in certain embodiments includes oral fluid sample.

The sample in certain embodiments includes exhaled breath sample.

The sample in certain embodiments includes a combination of oral fluid sample and exhaled breath sample.

In certain embodiments, the first substance detection routine and the second substance detection routine are performed simultaneously.

In certain embodiments, the first substance detection routine and the second substance detection routine are performed sequentially.

In certain embodiments, the target substance include cannabis.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample. Further, in certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the sample acquisition is performed using one or more of mass spectrometry, gas chromatography mass spectrometry, high pressure mass spectrometry, liquid chromatography mass spectrometry, or two dimensional gas chromatography mass spectrometry.

A method in still a further embodiment includes performing acquisition of a sample having one or more analysis substances, executing, using one or more processors, a first substance detection routine for detecting the presence of the first analysis substance, a second substance detection routine for detecting the presence of the first analysis substance, and a third substance detection routine for detecting the presence of the second analysis substance, and generating an output signal based on the executed first, second and third substance detection routines, wherein the output signal corresponds to the presence in the sample of target substance associated with the one or more of the analysis substances, where the second substance detection routine is performed within a predetermined time period after the completion of the first substance detection routine and further where the output signal confirms acute detection of the target substance in the acquired sample when (1) a determined gradient of the first analysis substance corresponds to a predetermined gradient profile, where the gradient is determined based on the level of the detected first analysis substance from the first substance detection routine and the second substance detection routine, and (2) the presence of the second analysis substance associated with the target sample from the third substance detection routine is determined.

The sample in certain embodiments includes oral fluid sample.

The sample in certain embodiments includes exhaled breath sample.

The sample in certain embodiments includes a combination of oral fluid sample and exhaled breath sample.

In certain embodiments, the first substance detection routine and the second substance detection routine are performed simultaneously.

In certain embodiments, the first substance detection routine and the second substance detection routine are performed sequentially.

In certain embodiments, the target substance include cannabis.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample. Further, in certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the sample acquisition is performed using one or more of mass spectrometry, gas chromatography mass spectrometry, high pressure mass spectrometry, liquid chromatography mass spectrometry, or two dimensional gas chromatography mass spectrometry.

An apparatus in accordance with one embodiment includes one or more sampling modules configured to acquire one or more samples having one or more analysis substances, a processing unit operatively coupled to the one or more sampling modules configured to execute a first substance detection routine and a second substance detection routine for detecting the presence of the first analysis substance and the second analysis substance in the acquired one or more samples, respectively, and an output unit operatively coupled to the processing unit and configured to output one or more signals based on the executed first and second substance detection routines, wherein the output signal corresponds to acute detection of target substance in the one or more samples.

In certain embodiments, the sample includes oral fluid sample.

In certain embodiments, the sample includes exhaled breath sample.

In certain embodiments, the sample includes a combination of oral fluid sample and exhaled breath sample.

In certain embodiments, the processing unit is configured to perform the first substance detection routine and the second substance detection routine simultaneously.

In certain embodiments, the processing unit is configured to perform the first substance detection routine and the second substance detection routine sequentially.

In certain embodiments, the target substance or substances include cannabis, alcohol, or cannabis and alcohol.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample.

In certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the first substance detection routine and the second substance detection routine are performed using one or more of mass spectrometry, gas chromatography mass spectrometry, high pressure mass spectrometry, liquid chromatography mass spectrometry, or two dimensional gas chromatography mass spectrometry.

In certain embodiments, the one or more sampling module includes a single use disposable cartridge.

An apparatus in accordance with still yet further embodiment includes one or more sampling modules configured to acquire one or more samples having one or more analysis substances, a processing unit operatively coupled to the one or more sampling modules configured to execute a first substance detection routine and a second substance detection routine for detecting the presence of the first analysis substance and the second analysis substance in the acquired sample, respectively to generate one or more signals based on the executed first and second substance detection routines, wherein the generated one or more signals corresponds to acute detection• of target substance in the one or more samples, where the second substance detection routine is performed within a predetermined time period after the completion of the first substance detection routine, where the first analysis substance is the same as the second analysis substance, and further, where the one or more signals confirms the acute detection of the target substance in the acquired sample when a determined gradient corresponds to a predetermined gradient, where the gradient is determined based on the level of the detected first analysis substance and the detected second analysis substance.

In certain embodiments, the sample includes oral fluid sample.

In certain embodiments, the sample includes exhaled breath sample.

In certain embodiments, the sample includes a combination of oral fluid sample and exhaled breath sample.

In certain embodiments, the processing unit is configured to perform the first substance detection routine and the second substance detection routine simultaneously.

In certain embodiments, the processing unit is configured to perform the first substance detection routine and the second substance detection routine sequentially.

In certain embodiments, the target substance or substances include cannabis, alcohol, or cannabis and alcohol.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample.

In certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the first substance detection routine and the second substance detection routine are performed using one or more of mass spectrometry, gas chromatography mass spectrometry, high pressure mass spectrometry, liquid chromatography mass spectrometry, or two dimensional gas chromatography mass spectrometry.

In certain embodiments, the one or more sampling module includes a single use disposable cartridge.

An apparatus in yet still a further embodiment includes one or more sampling modules configured to acquire one or more samples having one or more analysis substances, a processing unit operatively coupled to the one or more sampling modules configured to execute a first substance detection routine for detecting the presence of the first analysis substance, a second substance detection routine for detecting the presence of the first analysis substance, and a third substance detection routine for detecting the presence of the second analysis substance, the processing unit further configured to generate an output signal based on the executed first, second and third substance detection routines, wherein the output signal corresponds to acute detection of target substance in the one or more samples, where the second substance detection routine is performed within a predetermined time period after the completion of the first substance detection routine, and further where the output signal confirms acute detection of the target substance in the acquired sample when (1) a determined gradient of the first analysis substance corresponds to a gradient profile, where the gradient is determined based on the level of the detected first analysis substance from the first substance detection routine and the second substance detection routine, and (2) the presence of the second analysis substance associated with the target sample from the third substance detection routine is determined.

In certain embodiments, the sample includes oral fluid sample.

In certain embodiments, the sample includes exhaled breath sample.

In certain embodiments, the sample includes a combination of oral fluid sample and exhaled breath sample.

In certain embodiments, the processing unit is configured to perform the first substance detection routine and the second substance detection routine simultaneously.

In certain embodiments, the processing unit is configured to perform the first substance detection routine and the second substance detection routine sequentially.

In certain embodiments, the target substance or substances include cannabis, alcohol, or cannabis and alcohol.

In certain embodiments, the plurality of analysis substances includes cannabinoid and one or more metabolites of cannabinoids. Further, in certain embodiments, the cannabinoid includes tetrahydrocannabinol (THC) and further, wherein the one or more metabolites includes cannabinol (CBN), 11-Hydroxy-$\Delta^9$-tetrahydrocannabinol (11-OH-THC), or 11-nor-9-Carboxy-THC (THC-COOH).

In certain embodiments, the output signal corresponds to acute presence of the target substance in the acquired sample indicating exposure of the sample to the target substance within a predetermined time period prior to obtaining the sample.

In certain embodiments, the predetermined time period includes one or more of less than 30 minutes from sample acquisition, between 30 minutes to one hour from sample acquisition, between one hour and two hours from sample acquisition, between two hours and three hours from sample acquisition, between three hours and four hours from sample acquisition, or more than four hours from sample acquisition.

In certain embodiments, the first substance detection routine and the second substance detection routine are performed using one or more of mass spectrometry, gas chromatography mass spectrometry, high pressure mass spectrometry, liquid chromatography mass spectrometry, or two dimensional gas chromatography mass spectrometry.

In certain embodiments, the one or more sampling module includes a single use disposable cartridge.

It will be apparent to those skilled in the art that various modifications and alterations in the methods, devices, and systems of the present disclosure will be apparent to those skilled in the art without departing from the scope and spirit of the present disclosure. Although the present disclosure has been described in connection with specific embodiments, it should be understood that the present disclosure as claimed should not be unduly limited to such specific embodiments. It is intended that the following claims define the scope of the present disclosure and that structures and methods within the scope of these claims and their equivalents be covered thereby.

What is claimed is:

1. An apparatus comprising:
   one or more sampling modules configured to receive one or more exhaled breaths and acquire therefrom a breath sample;
   a processing unit operatively coupled to the one or more sampling modules and configured to execute a first substance detection routine for detecting a level of alcohol in the breath sample and a second substance detection routine for detecting a level of one or more cannabinoids in the breath sample; and
   an output unit operatively coupled to the processing unit and configured to output one or more signals based on the level of alcohol detected in the breath sample by the first substance detection routine and the level of the one or more cannabinoids detected in the breath sample by the second substance detection routine.

2. The apparatus of claim 1, wherein the one or more sampling modules includes a first sampling module configured to be used by the first substance detection routine and a second sampling module configured to be used by the second substance detection routine.

3. The apparatus of claim 1, further comprising a data communications unit operatively coupled with the processing unit and configured to transfer data from the first substance detection routine and the second substance detection routine from the apparatus to another, separate device.

4. The apparatus of claim 1, wherein:
   the processing unit is located in a housing, and
   at least one of the one or more sampling modules is located in a cartridge that is configured to be releasably mated to the housing.

5. The apparatus of claim 4, wherein the cartridge includes an inlet vent configured to be placed in a person's mouth to facilitate breath sample collection when the person exhales.

6. The apparatus of claim 1, wherein the second substance detection routine is for detecting the level of one or more cannabinoids selected from the group consisting of: tetrahydrocannabinol (THC), cannabinol (CBN), 11-Hydroxy-$\Delta^9$-tetrahydrocannabinol (11OH-THC), 11-nor-9-Carboxy-THC (THC-COOH), and one or more metabolites of cannabis.

7. The apparatus of claim 1, wherein:
   the second substance detection routine is for detecting the level of tetrahydrocannabinol (THC),
   the processing unit is further configured to execute a third substance detection routine, and
   the third substance detection routine is for detecting a metabolite of THC.

8. The apparatus of claim 1, wherein:
   the second substance detection routine is for detecting the level of a first metabolite of tetrahydrocannabinol (THC),
   the processing unit is further configured to execute a third substance detection routine, and
   the third substance detection routine is for detecting a second metabolite of THC different from the first metabolite of THC.

9. The apparatus of claim 1, wherein the second substance detection routine is selected from the group consisting of: mass spectrometry, gas chromatography mass spectrometry, high-pressure mass spectrometry, liquid chromatography mass spectrometry, and two-dimensional gas chromatography mass spectrometry.

10. The apparatus of claim 1, wherein the processing unit is configured to execute the first substance detection routine and the second substance detection routine simultaneously or sequentially.

11. A method comprising:
   receiving one or more exhaled breaths in one or more sampling modules to acquire therefrom a breath sample;
   executing a first substance detection routine for detecting a level of alcohol in the breath sample;
   executing a second substance detection routine for detecting a level of one or more cannabinoids in the breath sample; and
   outputting one or more signals based on the level of alcohol detected in the breath sample by the first substance detection routine and the level of the one or more cannabinoids detected in the breath sample by the second substance detection routine.

12. The method of claim 11, further comprising:
   using a first sampling module of the one or more sampling modules during the first substance detection routine and using a second sampling module of the one or more sampling modules during the second substance detection routine.

13. The method of claim 11, further comprising transferring data from the first substance detection routine and the second substance detection routine from an apparatus including the one or more sampling modules to another, separate device.

14. The method of claim 11, further comprising mating a cartridge including at least one of the one or more sampling modules to a housing containing a processing unit configured to execute the first substance detection routine and the second substance detection routine.

15. The method of claim 14, wherein the cartridge includes an inlet vent and the method further comprises placing the inlet vent in a person's mouth to collect the breath sample when the person exhales.

16. The method of claim 11, wherein the second substance detection routine is for detecting the level of one or more cannabinoids selected from the group consisting of: tetrahydrocannabinol (THC), cannabinol (CBN), 11-Hydroxy-$\Delta^9$-tetrahydrocannabinol (11OH-THC), 11-nor-9-Carboxy-THC (THC-COOH), and one or more metabolites of cannabis.

17. The method of claim 11, further comprising executing a third substance detection routine for detecting a level of one or more metabolites of tetrahydrocannabinol (THC) in the breath sample, wherein:
   the second substance detection routine is for detecting the level of tetrahydrocannabinol (THC), and
   the third substance detection routine is for detecting a metabolite of THC.

18. The method of claim 11, further comprising executing a third substance detection routine, wherein:
   the second substance detection routine is for detecting the level of a first metabolite of tetrahydrocannabinol (THC) in the breath sample, and
   the third substance detection routine is for detecting a second metabolite of THC different from the first metabolite of THC.

19. The method of claim 11, wherein the second substance detection routine is selected from the group consisting of: mass spectrometry, gas chromatography mass spectrometry, high-pressure mass spectrometry, liquid chromatography mass spectrometry, and two-dimensional gas chromatography mass spectrometry.

20. The method of claim 11, wherein the first substance detection routine and the second substance detection routine are executed simultaneously or sequentially.

* * * * *